(12) United States Patent
Molitor et al.

(10) Patent No.: US 9,598,339 B2
(45) Date of Patent: Mar. 21, 2017

(54) PREPARATION AND USE OF CYCLODODECATRIENE TRIALDEHYDE AND RELATED COMPOUNDS

(71) Applicant: Dow Global Technologies LLC, Midland, MI (US)

(72) Inventors: Erich J. Molitor, Midland, MI (US); Robert E. Hefner, Jr., Rosharon, TX (US)

(73) Assignee: Dow Global Technologies LLC

( * ) Notice: Subject to any disclaimer, the term of this patent is extended or adjusted under 35 U.S.C. 154(b) by 0 days.

(21) Appl. No.: 15/078,655

(22) Filed: Mar. 23, 2016

(65) Prior Publication Data

US 2017/0022134 A1    Jan. 26, 2017

Related U.S. Application Data

(62) Division of application No. 14/375,325, filed as application No. PCT/US2013/027242 on Feb. 22, 2013, now Pat. No. 9,328,193.

(60) Provisional application No. 61/602,840, filed on Feb. 24, 2012.

(51) Int. Cl.
| | |
|---|---|
| C08G 14/02 | (2006.01) |
| C07C 45/50 | (2006.01) |
| C08G 8/04 | (2006.01) |
| C08G 59/62 | (2006.01) |

(52) U.S. Cl.
CPC ............. *C07C 45/50* (2013.01); *C08G 8/04* (2013.01); *C08G 59/621* (2013.01); *C07C 2101/20* (2013.01)

(58) Field of Classification Search
CPC ....... C07C 37/20; C07C 39/17; C07C 261/02; C07C 2101/14
USPC .................................................. 528/86, 165
See application file for complete search history.

(56) References Cited

U.S. PATENT DOCUMENTS

| | | |
|---|---|---|
| 3,089,904 A | 5/1963 | Lippincott et al. |
| 3,184,432 A | 5/1965 | Gunther et al. |
| 3,312,742 A | 4/1967 | Wolfgang et al. |
| 3,354,229 A | 11/1967 | Leveme et al. |
| 4,251,462 A | 2/1981 | Braden et al. |
| 4,438,241 A | 3/1984 | Mark et al. |
| 4,554,330 A | 11/1985 | Mark et al. |
| 5,138,101 A | 8/1992 | Devon |
| 5,736,620 A | 4/1998 | Earls et al. |
| 6,133,190 A | 10/2000 | Wehmeyer et al. |
| 6,252,121 B1 | 6/2001 | Argyropoulos et al. |
| 6,307,108 B1 | 10/2001 | Argyropoulos et al. |
| 7,683,219 B1 | 3/2010 | Hsueh et al. |

(Continued)

OTHER PUBLICATIONS

Adlington, et al. Azo anions in synthesis. t-Butylhydrazones as acyl-anion equivalents. Journal of the Chemical Society Chemical Communications. Issue 18, p. 1040. 1983.

(Continued)

*Primary Examiner* — Shane Fang

(57) ABSTRACT

Disclosed herein are compositions and methods related to the hydroformylation of cyclododecatriene to form cyclododecatriene trialdehyde, and the conversion of the trialdehyde to the polyphenols of Formula 1:

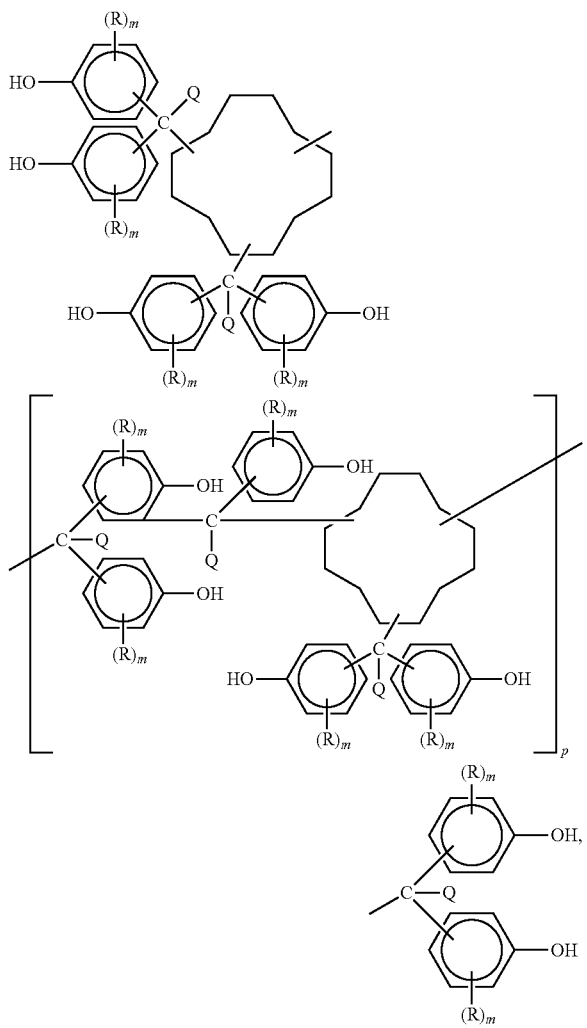

where R, m p and Q are as defined herein. Curable compositions comprising compounds of Formula 1, including powder coating compositions, and methods of curing the compositions are also disclosed.

4 Claims, No Drawings

(56) References Cited

U.S. PATENT DOCUMENTS 8,609,788 B2    12/2013  Hefner et al.
8,729,181 B2     5/2014  Mullins et al.

OTHER PUBLICATIONS

Hirao, et al. Oxidative nucleophilic addition of organovanadium reagents to aldehyes with formation of ketones. Journal of the American Chemical Society. 107, 7179. Nov. 1985.
Hirao, et al. Versatile synthesis of a, B-acetylenic ketones by oxidative nucleophilic addition of vanadium acetyhdes. Tetrahedron Letters. Volume 27, p. 933. 1986.
Itsuno, et al. Reaction of aldehyde O-alkyl oxime with organometallic compounds. Tetrahedron Letters. Volume 27, p. 3033. 1986.
Byrne, et al. Magnesium-oppenauer oxidation of alcohols to aldehydes and ketones. Tetrahedron Letters. vol. 28, p. 769. 1987.
Longoni, et al. Hydroformylation of hydrocarbonylation of dicyclopentadiene with cobalt-rhodium catalytic systems promoted by triphenylphosphine: sythesis of monoformyltricyclodcenes, diformyltricyclodecanes and di(tricyclodecenyl ketones. Journal of Molecular Catlysis. Volume 68, p. 7-21. 1991.
Kirk-Othmer, Encyclopedia of Chemical Technology, 5th Edition, vol. 10. Oxo Process, pp. 1-17, 2000.
Lee, et al. Handbook of Epoxy Resins, Copyright 1967, pp. 2-6 through 2-9 and pp. 11-13 through 11-14.

PREPARATION AND USE OF CYCLODODECATRIENE TRIALDEHYDE AND RELATED COMPOUNDS

FIELD OF THE INVENTION

Disclosed herein is a method of hydroformylating cyclododecatriene (CDDT) in the presence of a rhodium catalyst to predominantly form the triformylated cyclododecane, and the subsequent manipulation of the resulting aldehyde groups.

BACKGROUND OF THE INVENTION

Phenolic resins are synthetic materials that vary greatly in molecular structure. This variety allows for a multitude of applications for these resins; for example, use as a curing agent and/or to prepare the corresponding epoxy, cyanate and/or allyl thermosettable resins. These curing agents and/or resins can provide enhanced physical and/or mechanical properties to a cured composition, such as increased glass transition temperature (Tg). To achieve improved properties, however, would require the resin to have a high level of functionality (i.e., chemical groups available for cross linking). As the level of functionality increases in these resins, so does their molecular weight. As the molecular weight increases, so does the melt viscosity of the resin, which can lead to difficulties in using such resins. Thus, work has been conducted on the preparation of the aldehydes of CDDT, which can be further manipulated to create new monomers, oligomers and/or polymers.

Hydroformylated CDDT has been a synthetic target for years because it is envisioned as useful in the preparation of polymers. However, hydroformylation of CDDT results in a mixture of mono, bis, and triformylated product, typically with the mono or bis formylated product dominating the product mixture. The triformylated product may be prepared, but in very poor yields. It is also very difficult to separate the mono, bis, and trialdehydes.

U.S. Pat. No. 3,089,904 used a cobalt catalyst to hydroformylate CDDT and while the desired products were the mono and bis formylated compounds, the triformylated compound may also have been prepared, possibly as a minor component.

U.S. Pat. No. 3,184,432 described the hydroformylation of CDDT using cobalt based catalysts and the conversion of the resulting mono, bis, or trialdehydes to the corresponding mono, bis, or trialcohols. The trialcohol was not isolated.

U.S. Pat. No. 3,312,742 disclosed the hydroformylation of CDDT using palladium or cobalt based compounds in conjunction with Adkins catalyst and the isolation of the resulting mono alcohol or mono formylated products.

U.S. Pat. No. 4,251,462 taught the hydroformylation of CDDT using a combination of a rhodium catalyst and a dicobalt catalyst to generate mono, bis and trialdehydes. Example 3 in this patent reported the preparation of a hydroformylated mixture comprising 13% bis aldehyde and 85% trialdehyde (as measured by gas chromatography; the aldehydes do not appear to have been separated), where the reaction was run at 160° C. and >4000 psig using 500 ppm rhodium catalyst. The aldehydes of this patent were then converted to the amines by reductive amination.

U.S. Pat. No. 5,138,101 disclosed an extraction method that enabled the separation of product of a rhodium catalyzed hydroformylation of CDDT from the rhodium containing reaction mixture. Two different hydroformylation reactions were run. In both reactions (see reference examples 2 and 15), mono, bis and triformylated products were formed, and in both reactions, the bis formylated compound was the major product, followed by the mono formylated compound, and then the triformylated product (amounts were based on GLC analysis of the reaction mixture.) Both reactions were also run at 125° C. and approximately 260 psi. After cooling, the reaction mixture was then extracted with an alcohol and water extraction mixture that preferentially extracts the products of the hydroformylation reaction from the rhodium containing reaction mixture.

U.S. Pat. No. 6,252,121 used phase separation to selectively separate the cyclic hydroformylation product from the reaction mixture and then distilled the product. Neither the hydroformylation of CDDT nor the purification of the resulting products was described.

U.S. Pat. No. 7,683,219 conducted a hydroformylation reaction in the presence of an aldehyde, which facilitated the phase separation of the hydroformylation product from the reaction mixture. Neither the hydroformylation of CDDT nor the purification of the resulting products was described.

Current methods of hydroformylating CDDT preferentially form the mono and bis aldehydes; the trialdehyde, if formed, is a minor product. The resulting products must then be separated, which is not a simple task. Or, higher yields of the trialdehyde may be formed, but under very forcing conditions using high temperature and pressure.

It would be beneficial to be able to prepare the trialdehyde of CDDT in high yield using mild conditions. This would minimize the need to purify the resulting product mixture, and facilitate the preparation of derivatives thereof for use in the preparation of monomers, oligomers, and polymers.

SUMMARY OF THE INVENTION

The inventors have surprisingly and unexpectedly invented a hydroformylation method for the selective preparation of the trialdehyde of cyclododecatriene that does not require a separate step to remove the mono and di aldehydes of cyclododecatriene.

In a first aspect, disclosed herein is a method of hydroformylating cyclododecatriene to form the trialdehyde, the method comprising:

a) preparing a first mixture comprising a rhodium compound and an organophosphite ligand in a solvent;

b) heating the first mixture in the presence of a gas comprising CO and $H_2$ to form a second mixture comprising an activated catalyst complex; and c) combining cyclododecatriene and the second mixture to form a third mixture.

In a second aspect, disclosed herein are compounds of Formula 1:

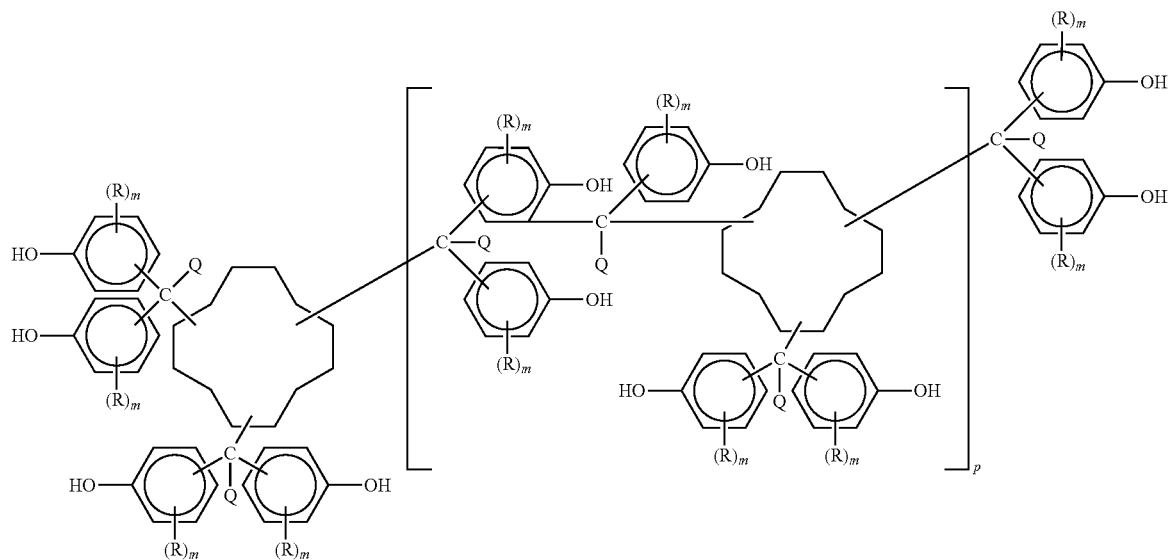

and methods of making such compounds, which are made by subjecting the cyclododecane trialdehyde to conditions sufficient to add two hydroxyaromatic groups per aldehyde or ketone.

In Formula 1, each m independently has a value of zero to 3, p has a value of zero to 20, preferably zero to 5, most preferably zero to 1; each R is independently halogen, preferably fluorine, chlorine or bromine; nitrile; nitro; $C_1$-$C_6$ alkyl or $C_1$-$C_6$ alkoxy preferably the alkyl and alkoxy groups independently have 1 to 4, most preferably 1 to 2 carbon atoms which may be substituted with one or more halogen atoms, preferably chlorine or bromine; or $C_2$-$C_6$ alkenyl or $C_2$-$C_6$ alkenyloxy, preferably the aforementioned alkenyl groups have 2 to 4, most preferably 2 to 3 carbon atoms; and each Q is independently hydrogen or $C_1$-$C_6$ alkyl, preferably the alkyl group has 1 to 4, most preferably 1 to 2 carbon atoms. Each R group may independently be a $C_3$-$C_4$ alkylene group that optionally contains one or two double bonds and is bonded to two adjacent carbons on the ring to which it is attached; thereby producing fused rings systems such as naphthyl, tetrahydronaphthyl, indenyl or indanyl.

It should be understood that the composition of the compounds of Formula 1 can be mixtures with various values of p. For such mixtures the values of p can be described as number average degrees of oligomerization.

For the various embodiments, when m has a value other than zero, the carbon bonded to Q

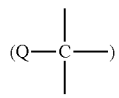

is preferably in the ortho and/or para position relative to the —OH group. It is appreciated that mixtures of compounds having the carbon bonded to the Q in both the ortho and the para position relative to the —OH group are possible. It is also possible to have the carbon bonded to Q

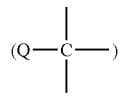

in the meta position relative to the —OH group.

In a third aspect, disclosed herein are methods of making compounds of Formula 1, the methods comprising subjecting the trialdehyde of CDDT to conditions sufficient to convert the aldehyde groups to the diphenolmethyl groups.

In another aspect, the aldehydes of Formulas 2a and 2b may be reduced to form the corresponding trialcohol and dialcohol compounds. Methods include using reducing agents, such as $LiAlH_4$, $NaBH_4$ or heterogeneous catalysts (such as those based on Pd, Pt or Ni) and hydrogen gas, optionally in the presence of a solvent. Other methods are known in the art.

The trialdehydes disclosed herein may be in a mixture comprising cyclododecane dialdehydes; thus, reduction of the mixture may result in the formation of the tri and dialcohols.

In another aspect, the trialdehyde compounds of Formulas 2a and 2b may be converted into the corresponding triamines. Methods include reductive amination in the presence of ammonia or a primary amine with either hydrogen and a metal catalyst, or a reducing agent, such as $NaCNBH_3$ or $NaBH_4$ optionally in the presence of a solvent. Other methods are known in the art. The trialdehydes disclosed herein may be in a mixture comprising cyclododecane dialdehydes; thus, reductive amination of the mixture will result in the formation of the triamine and the diamine.

Formula 2a

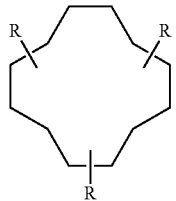

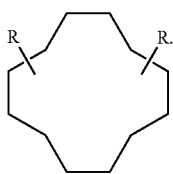

Formula 2b

Where each R group is independently CHO, CH$_2$OH, or CH$_2$NH$_2$, and the cyclododecane ring in Formula 2b is saturated or unsaturated.

Also disclosed are curable compositions that includes the compounds of Formula 1 and a curing amount of a resin, such as an epoxy resin, and/or a catalytic amount of a catalyst and/or a cure accelerating amount of an accelerating agent. The curable composition can also include a CDDT diphenol, tetraphenol and/or an oligomer of the cyclododecane polyphenol. For the various embodiments, the cyclodecane polyphenols of Formula 1 can be used in forming a cured or a partially cured (B-staged) composition.

DETAILED DESCRIPTION OF THE INVENTION

As described above, in a first aspect, disclosed herein is a method of hydroformylating cyclododecatriene to preferentially form the trialdehyde.

In one embodiment, the method utilizes a rhodium compound. Various rhodium compounds may be used, such as RhCl$_3$ xH$_2$O, (RhCl(CO)$_2$)), Rh$_6$(CO)$_{16}$, Rh$_4$(CO)$_{12}$, (RhNO$_3$)$_3$, and Rh(CO)$_2$(AcAc), where x is the number of water molecules associated with the RhCl$_3$. In one embodiment, Rh(CO)$_2$(AcAc) is preferred.

Organophosphites that may be used in the hydroformylation reaction include triphenylphosphite, tris(3-methyl-6-tert-butylphenyl) phosphite, tris(2,4-di-tert-butylphenyl) phosphite, di(2-tert-butylphenyl)-tert-butylphosphite, tri (C$_1$-C$_6$)alkyl phosphine or other suitable phosphorus-containing organics. In one embodiment, tris(2,4-di-tert-butylphenylphosphite is preferred.

Various solvents may be used when conducting the hydroformylation reaction. Preferred solvents are apolar and aprotic, such as C$_5$-C$_{10}$ hydrocarbons, which include alkanes, cycloalkanes, and aromatics such as benzene, toluene, and xylene. In one embodiment, hexanes and heptanes are particularly preferred with heptanes (either a mixture of isomers or predominantly n-heptane) being most preferred.

The molar ratio of rhodium compound to organophosphite is from 10:1 to 1:10. More preferably, the ratio is 5:1 to 1:9. Still more preferably, the organophosphite is used in excess. Ratios of 1:5 to 1:9 being preferred.

Once the rhodium compound, organophosphite ligand and the solvent are combined, the activated catalyst complex is formed by adding a gas comprising CO and H$_2$. The ratio of the CO to H$_2$ in the gas is 100:1 to 1:100. More preferably, the ratio is 50:1 to 1:50. Still more preferably, the ratio is 10:1 to 1:10; even more preferred the ratio is 1:1 (known as syn gas).

The reaction may be conducted in a high pressure reactor, such as a Paar reactor or a similar device.

Before beginning to heat the first reaction mixture, it is advisable, although not required, to purge the reaction vessel several times (such as 3 times) with the CO and H$_2$ gas combination.

When heating the first mixture in the presence of a gas comprising CO and H$_2$ to form a second mixture, the pressure in the reaction vessel is 70 psig to 2200 psig. In further embodiments, it is 300 to 800 psig, with 400 to 700 psig more preferred and a pressure of 550 to 650 psig still more preferred and a pressure of about 600 psig being most preferred. It is believed that higher pressures should facilitate the hydroformylation reaction.

The reaction may be stirred, agitated or otherwise mechanically mixed in order to ensure mixing of the reaction components.

The first mixture is heated to temperatures of 50 to 120° C. (the reaction temperature is dependent on the solvent used and the pressure in the reaction container). More preferably the reaction is run at 70 to 100° C.; still more preferably the reaction temperature is 75 to 85° C.; even more preferably, the reaction temperature is 80° C.

The hydroformylation reaction time is typically 4 to 24 hours. More preferably, it is 6 to 12 hours. Still more preferably, it is 8 to 10 hours, with 9 hours being typical. In one aspect, the reaction is run at 80° C. for 9 hours.

After the reaction is complete as determined using GC analysis or any other method known to those skilled in the art, the reaction mixture is allowed to cool to room temperature. Then the cyclododecane trialdehyde (typically the lower layer, but this is solvent dependent) is separated from the third mixture and optionally washed with a C$_5$-C$_{10}$ hydrocarbon that is typically the same as the reaction solvent.

GC analysis of the resulting reaction product shows it contains greater than 90% trialdehyde, which is higher than any previously reported yield.

The cyclododecatriene may be added to the second mixture or the second mixture may be added to the cyclododecatriene. Adding the cyclododecatriene to the second mixture is preferred.

After removing the trialdehyde from the third mixture, the remaining rhodium catalyst, organophosphite and heptanes may be used to catalyze another hydroformylation of cyclododecatriene.

In an embodiment, the rhodium catalyst is Rh(CO)$_2$(AcAc), the organophosphite is tris(2,4-di-tert-butylphenylphosphite, used in excess, the solvent is heptanes, the first mixture is treated with a 1:1 mixture of CO and H$_2$ at a pressure of 200 psig for a time sufficient to activate the catalyst complex, and after adding the CDDT, the reaction is run at 80° C. for 9 hours.

The cyclododecane polyphenols of the present disclosure can be produced from cyclododecane aldehydes and/or ketones. For the various embodiments, trialdehydes can be produced via hydroformylation of CDDT using syngas, a phosphine ligand, and a transition metal (from Groups 3 through 10) catalyst using a method such as described by G. Longoni, et al, J. of Molecular Catalysis 68, 7-21 (1991) or more generally in Kirk-Othmer, ENCYCLOPEDIA OF CHEMICAL TECHNOLOGY, Fifth Edition, Vol. 10, pp. 347-470 (2010). There are many variations in this process, including a method (U.S. Pat. No. 6,307,108 B1) that uses mixed polar/nonpolar solvents to ease the problem of catalyst recycle and product separation. The resulting cyclododecane aldehydes can then be condensed with phenol to form the polyphenols.

Disclosed herein are cyclododecane polyphenols that are useful as curing agents for epoxy resins and/or as precursors to thermoset resins. The polyphenols of the present disclosure may provide high level functionality (at least four functional groups/molecule with at least six functional groups per molecule being more preferred) when used in a curable composition. Surprisingly, however, the weight average molecular weights of these polyphenols may be relatively low. As a result, melt viscosities of curable compositions that include the polyphenols disclosed herein may be lower than those utilizing compounds having comparable or even lower level of functionality.

For the various embodiments, the polyphenols of the present disclosure may be formed from the trialdehydes which may additionally contain cyclododecanemonoaldehydes and/or dialdehydes. The use of trialdehydes containing monoaldehydes and/or dialdehydes may allow for the polyphenols of the present disclosure to achieve a high level of functionality with a relatively low molecular weight, which may allow for a relatively low melt viscosity of the curable composition.

When hydroformylating the CDDT to form the trialdehyde, minor amounts of partially or totally saturated CDDT monoaldehydes and/or dialdehydes may also be produced. Preferably, 30 weight percent or less (more preferably, 15 weight percent or less, still more preferably, 10 weight percent or less) of the reaction product is partially or totally saturated monoaldehydes and/or dialdehydes. As a result, the trialdehyde is typically in a mixture having the same or similar product ratios as the reaction product. In preferred mixtures, the trialdehyde is at least 86 weight percent and the dialdehyde comprises less than 10 weight percent of the product. More preferably, the trialdehyde is greater than 90 (more preferably, greater than 91) weight percent and the dialdehyde is less than 9 (more preferably less than 8) weight percent of the product.

An example of these saturated dialdehydes with saturated cyclododecane ring is represented by Formula 2b, wherein the R group is CHO.

The monoaldehydes and dialdehydes can be partially or totally separated from the trialdehydes. For example, distillation or column chromatography could be used.

In an additional embodiment, various weight percents of the monoaldehydes and/or dialdehydes with partially or totally saturated cyclododecane ring could also be mixed with the trialdehydes. Using mixtures containing the monoaldehydes and/or the dialdehydes may allow for control of the level of functionality in the resulting curable composition. Thus, mixtures of CDDT diphenols and/or CDDT tetraphenols with cyclododecane hexaphenols plus oligomers, if any, may be produced as an additional embodiment of the present disclosure. An example of the CDDT tetraphenols with saturated cyclododecane ring is represented by the following Formula 3, where p=0 and m, R and Q are as described herein.

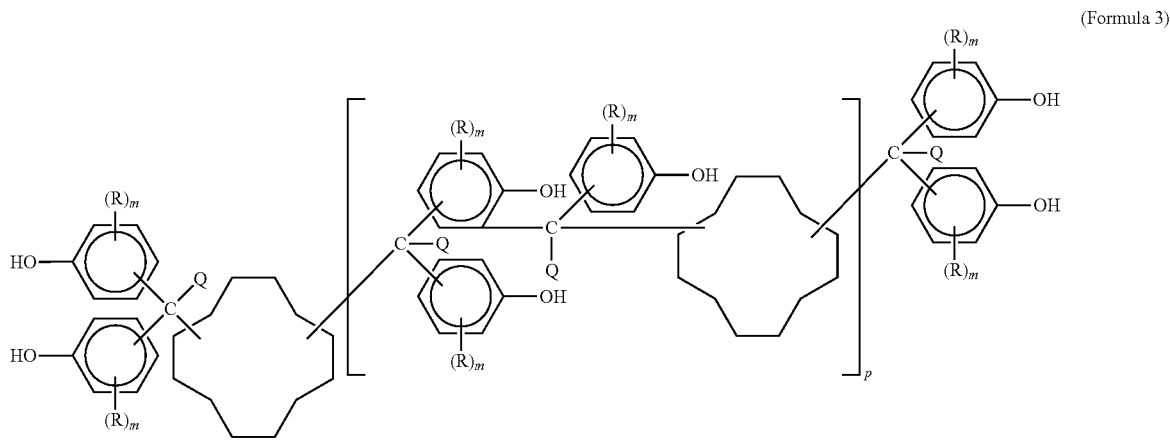

(Formula 3)

Hydroformylation can also produce small amounts of isomeric ketones as described by Longoni. These ketones can be the predominant products when the $H_2/CO$ pressure is low (~1 atm). If these ketones are present in the product mix they can be condensed with phenol to form polyphenols of Formula 4, where p, m, and R are as described herein:

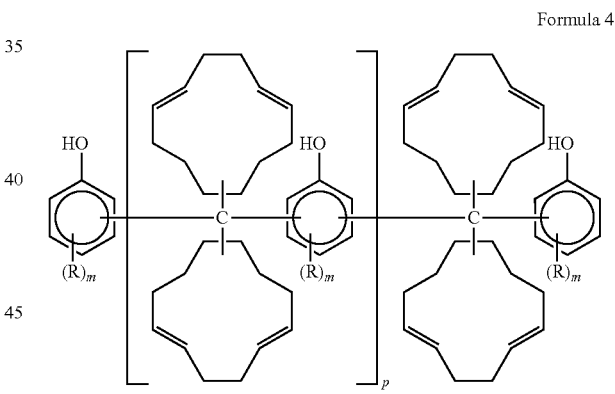

Formula 4

For the various embodiments, CDDT mono and diketones and cyclododecane triketones useful in the present disclosure to prepare compositions of Formula 1 where Q is an alkyl group can be produced through a multistep synthesis, for example the chemistry given in Tetrahedron Letters, 28, 769 (1987); Tetrahedron Letters, 27, 3033 (1986); Tetrahedron Letters, 27, 933 (1986); Journal of the American Chemical Society, 107, 7179 (1985); and Journal of the Chemical Society: Chemical Communications, 1040 (1983).

Curable compositions formed with the polyphenols may also provide for cured compositions that have an enhanced glass transition temperature (Tg). Additionally, it is expected that the polyphenols will also provide improvements in both moisture resistance and corrosion resistance, as well as enhanced electrical properties, of the cured composition, especially dissipation factor.

As mentioned above, in one aspect, the trialdehydes (or mixtures containing said trialdehydes) are converted to polyphenol compounds of Formula 1, which are useful as a monomer that may be used to make oligomers or polymers. Examples of other monomers, oligomers or polymers that may be made using this monomer include polyurethanes, polyethers, polyesters, epoxy resins, polycyanates, vinylbenzyl ethers, ethylenically unsaturated ethers such as allyl ethers and combinations thereof. Certain of these compositions are also useful for making powder coatings, electrical laminates and composites for aerospace.

As previously mentioned, the phenolic rings in Formula 1 may be substituted. In one preferred embodiment, the phenolic rings are unsubstituted, where Q and p are as hereinbefore defined.

In another preferred embodiment, the phenolic rings are unsubstituted, Q is hydrogen, and p is as hereinbefore defined.

In another aspect, disclosed herein is a method of making compounds of Formula 1 from the trialdehydes of cyclododecane.

While various methods are known for introducing the diphenolmethyl group, including the use of protection and deprotection strategies, one preferred method is as follows.

The trialdehydes are reacted with an optionally substituted phenol (as described herein) in the presence of a catalyst. A solvent may be used, but preferably, the phenol is molten phenol.

The polyphenols are prepared via a condensation reaction of a mole ratio of the trialdehydes (and any dialdehydes and monoaldehydes) to phenol and/or substituted phenol, o-cresol, m-cresol, p-cresol, 2,4-dimethylphenol; 2,6-dimethylphenol; 1-naphthol and 2-naphthol of 1:20 to 1:6, and preferably from 1:15 to 1:8; in the presence of an acid catalyst which is preferably from 0.1 to 2, and more preferably from 0.1 to 1 wt. % based on the amount of phenol and/or substituted phenol compound employed. Higher mole ratios than 1:20 of the phenol and/or substituted phenol may be employed, however doing so may require additional energy and thus expense to recover and recycle the excess phenol or substituted phenol.

Condensation reactions employing a large excess of the phenol and/or substituted phenol (and curing agents and/or curing catalysts) have been found to favor polyphenols having a low polydispersity and weight average molecular weight. Likewise, as the amount of the phenol and/or substituted phenol is reduced, there can be an increase in oligomers of the cyclododecane polyphenols, increasing the weight average molecular weight. Increased oligomer content favors higher hydroxyl level of functionality per molecule which may be highly beneficial for certain end uses, for example, increasing the Tg, but at the cost of higher viscosity. Thus, while very large excesses of phenol and/or substituted phenol may be used, the present disclosure in one embodiment employs the molar ratio provided above to produce products rich in hexaphenols, and low in oligomers.

The condensation reaction to form the polyphenols of the present disclosure can also optionally include the use of a solvent. For these embodiments, asolvent inert to the reaction and reaction products may also be employed, such as, for example, toluene or xylene. The solvent may additionally serve as an agent for the azeotropic removal of water from the condensation reaction. With certain phenolic reactants with higher melt viscosities, use of one or more solvents may be beneficial for maintaining a suitable reaction medium.

Suitable acid catalysts include the protic acids, such as hydrochloric acid, sulfuric acid, phosphoric acid; metal oxides, such as zinc oxide, aluminum oxide, magnesium oxide; organic acids, such as p-toluenesulfonic acid, oxalic acid, 3-mercapto-1-propane sulfonic acid and combinations thereof. For the various embodiments, 3-mercapto-1-propane sulfonic acid is a preferred acid catalyst or co-catalyst. If desired, the 3-mercapto-1-propane sulfonic acid may be attached to a solid support, as in U.S. Pat. No. 6,133,190. Surprisingly, it has been found that 3-mercapto-1-propane sulfonic acid is so highly active and selective in forming the polyphenols that there is no need for an azeotropic removal of water from the reaction products. Rather, the water remains in the reactor, without quenching the phenolation reaction. Reaction temperatures and times vary, but can be from 5 minutes to 48 hours and reaction temperatures of from 20° C. to 175° C. may be employed. Preferably reaction temperatures and times can be from 15 minutes to 36 hours and reaction temperatures of from 30° C. to 125° C. Most preferably reaction temperatures and times can be from 30 minutes to 24 hours and reaction temperatures of from 35° C. to 75° C.

At the end of the reaction, the acidic catalyst can be removed by neutralization, for example, and/or by washing or extraction with water. Likewise, at the end of the reaction, excess phenol can be removed from the phenolated product, for example, by distillation or extraction.

For the various embodiments, the polyphenols of the present disclosure can have a polydispersity index (PDI, which is known in the art as a measure of distribution of molecular mass in a given polymer sample) of less than 2. For example, the PDI of the polyphenols can be from 1.3 to 1.4. These types of results indicate that the p values of each of the polyphenols for the present disclosure are very uniform. This result is surprising, as phenolation reactions often times produce products having a much larger polydispersity (e.g., from 2 to 5). Having a uniform chain length for the polyphenols disclosed herein allow for more desirable viscosity predictability in the viscosity of the curable compositions.

The polydispersity values for certain of the cyclododecane polyphenols are indicative of an increase in the level of functionality without substantial increase in Mw. High level of functionality and the resultant high crosslink density can provide very desirable high Tg.

For the various embodiments, starting with the trialdehydes allows for a high (i.e., greater than 2, more preferably greater than 3, still more preferably greater than 4, even more preferably 5 or more functional groups per molecule) level of functionality to be achieved in the resulting polyphenols without a large increase in the compound's Mw. This is not the case with previous attempts to form polyphenols with high levels of functionality. For example, embodiments of the present disclosure provide for functionalities of 6 hydroxyl groups with equivalent weights as low as 128 grams per hydroxyl equivalent. Embodiments described herein also allow for a scalable progression in the level of functionality to be achieved without significant increases in the molecular weight and viscosity of the curable composition.

The catalyst may be added in one portion, portionwise or continuously. If added portionwise, the portions may be of the same size, but need not be so. Catalyst portions may be added so as to control one or more parameters of the reaction such as reaction temperature.

After the reaction is completed, the unreacted phenol, which is typically used in excess, is removed using methods known in the art, such as by heating and applying a vacuum. The resulting solid product may be washed with water repeatedly until the phenol content no longer decreases, as determined by HPLC, GC or other type of analysis as known in the art. If desired, the resulting solid may be dried in a vacuum oven or using other means known in the art.

The product may be further purified using methods such as preparative HPLC or column chromatography, or it may be used as is.

As noted above, the compounds of Formula 1 may be used to make a powder coating composition. Methods known in the art may be used. For example, the components of the powder coating composition described herein are typically pre-blended or ground in a grinder, and the resulting mixture exiting from the grinder is then fed into an extruder.

In the extruder, the powder mixture is heated at low temperature and melted into a semi-liquid form. During this process, the components of the molten mixture are thoroughly and uniformly dispersed. Because of the fast operation of the extruder and the relatively low temperature within the extruder, the components of the powder coating compositions described herein will not undergo a significant chemical reaction. The resulting molten extrudate of the powder coating compositions described herein exit from the extruder and are then passed from the extruder onto a flaker, which then feeds the flakes of the composition into a mill/classifier to obtain a powder coating final product with a desired particle size. The final powder coating product is then packaged in closed containers, using a packaging unit to avoid moisture ingression into the product. The apparatus for manufacturing the powder coating composition described herein, such as the pre-blending station or grinder; the extruder, the flaker, the mill/classifier, and the packaging unit are all well known equipment in the art. The powder coating compositions described herein may be applied to a substrate by various methods. For example, in one embodiment, the powder coating composition may be applied to a substrate by (1) heating the substrate to a suitable curing temperature for the composition and (2) applying the powder coating composition by known means such as an electrostatic spray or a fluidized bed. In another embodiment, the powder coating composition may be applied to a cold substrate by (1) applying the powder coating composition to the substrate (e.g. with an electrostatic application method); and (2) heating the powder and the substrate to a temperature at which the powder flows and cures.

In some embodiments, powder coatings may be formed by applying a thermosettable resin composition to a substrate and then curing the curable thermosettable resin composition.

Curing of the thermosettable resin compositions disclosed herein usually requires a temperature of at least 30° C., up to 250° C., for periods of minutes up to hours, depending on the thermosettable resin used, the curing agent used, and the catalyst, if used. In other embodiments, curing may occur at a temperature of at least 100° C., for periods of minutes up to hours. Post-treatments may be used as well, such post-treatments ordinarily being at temperatures between 100° C. and 200° C.

For example, the curing reaction of the thermosettable composition may be conducted at a temperature, generally, between 20° C. and 250° C., preferably between 50° C. and 200° C., more preferably between 50° C. and 150° C. The time of curing the thermosettable resin composition may be for a predetermined period of time which can range from minutes up to hours, generally the reaction time is more than 1 minute and less than 24 hours, preferably between 5 minutes and 6 hours, and more preferably between 10 minutes and 2 hours. The curing conditions of the thermo-settable resin can also depend on the components used, and any optional components added to the composition such as a catalyst, if used. In other embodiments, partial curing may occur at a first temperature followed by a second temperature or post-treatment, such post-treatments ordinarily being at temperatures above 100° C., preferably between 100° C. and 200° C.

Thermoset resins may be formed by curing the curable thermosettable resin compositions described herein. The resulting thermoset resins may comprise a thermoset or a thermoset network structure with fillers and/or other additives. The term "thermoset" or "thermoset network structure" used herein refers to a substantially cured and cross-linked thermoset resin structure.

The resulting powder coatings display excellent thermo-mechanical properties, such as good toughness and mechanical strength, while maintaining high thermal stability.

Curable resin compositions may comprise compounds of Formula 1 and at least one curing agent. Optionally, one or more catalysts and/or other additives may also be included. In one embodiment, the curing agent is an epoxy resin having an average of more than one epoxide group per molecule. The epoxide group can be attached to an oxygen, a sulfur or a nitrogen atom or the single bonded oxygen atom attached to the carbon atom of a —CO—O— group. The oxygen, sulfur, nitrogen atom, or the carbon atom of the —CO—O— group may be attached to an aliphatic, cycloaliphatic, polycycloaliphatic or aromatic hydrocarbon group. The aliphatic, cycloaliphatic, polycycloaliphatic or aromatic hydrocarbon group can be substituted with an inert substituents including, but not limited to, halogen atoms, preferably fluorine, bromine or chlorine; nitro groups; or the groups can be attached to the terminal carbon atoms of a compound containing an average of more than one —(O—CHR$^a$—CHR$^a$)$_t$— group, where each R$^a$ is independently a hydrogen atom, an alkyl, or a haloalkyl group containing from one to two carbon atoms, with the proviso that only one R$^a$ group can be a haloalkyl group, and t has a value from one to about 100, preferably from one to about 20, more preferably from one to about 10, and most preferably from one to about 5.

More specific examples of the epoxy resin which can be used include diglycidyl ethers of 1,2-dihydroxybenzene (catechol); 1,3-dihydroxybenzene (resorcinol); 1,4-dihydroxybenzene (hydroquinone); 4,4'-isopropylidenediphenol (bisphenol A); 4,4'-dihydroxydiphenylmethane; 3,3',5,5'-tetrabromobisphenol A; 4,4'-thiodiphenol; 4,4'-sulfonyldiphenol; 2,2'-sulfonyldiphenol; 4,4'-dihydroxydiphenyl oxide; 4,4'-dihydroxybenzophenone; 1,1'-bis(4-hydroxyphenyl)-1-phenylethane; 3,3'-5,5'-tetrachlorobisphenol A; 3,3'-dimethoxybisphenol A; 4,4'-dihydroxybiphenyl; 4,4'-dihydroxy-alpha-methylstilbene; 4,4'-dihydroxybenzanilide; 4,4'-dihydroxystilbene; 4,4'-dihydroxy-alpha-cyanostilbene; N,N'-bis(4-hydroxyphenyl)terephthalamide; 4,4'-dihydroxyazobenzene; 4,4'-dihydroxy-2,2'-dimethylazoxybenzene; 4,4'-dihydroxydiphenylacetylene; 4,4'-dihydroxychalcone; 4-hydroxyphenyl-4-hydroxybenzoate; dipropylene glycol; poly(propylene glycol); thiodiglycol; the triglycidyl ether of tris(hydroxyphenyl)methane; the polyglycidyl ethers of a phenol or alkyl or halogen substituted phenol-aldehyde acid catalyzed condensation product (novolac resins); the tetraglycidyl amines of 4,4'-diaminodiphenylmethane; 4,4'-diaminostilbene; N,N'-dimethyl-4,4'-diaminostilbene; 4,4'-diaminobenzanilide; 4,4'-diaminobiphenyl; the polyglycidyl ether of the condensation product of a dicyclopentadiene or an oligomer thereof and a phenol or alkyl or halogen substituted phenol; and combinations thereof.

The epoxy resin which can be used may also include an advanced epoxy resin. The advanced epoxy resin may be a product of an advancement reaction of an epoxy resin with an aromatic di- and polyhydroxyl, or carboxylic acid containing compound. The epoxy resin used in the advancement reaction may include one or more of the aforesaid epoxy resins.

Preparation of the aforementioned advanced epoxy resin products can be performed using known methods, for example, an advancement reaction of an epoxy resin with one or more suitable compounds having an average of more than one reactive hydrogen atom per molecule, where the reactive hydrogen atom is reactive with an epoxide group in the epoxy resin. The ratio of the compound having an average of more than one reactive hydrogen atom per molecule to the epoxy resin is generally from about 0.01:1 to about 0.95:1, preferably from about 0.05:1 to about 0.8:1, and more preferably from about 0.10:1 to about 0.5:1 equivalents of the reactive hydrogen atom per equivalent of the epoxide group in the epoxy resin.

In addition to the aforementioned dihydroxyaromatic and dicarboxylic acid compounds, examples of the compound having an average of more than one reactive hydrogen atom per molecule may also include dithiol, disulfonamide or compounds containing one primary amine or amide group, two secondary amine groups, one secondary amine group and one phenolic hydroxy group, one secondary amine group and one carboxylic acid group, or one phenolic hydroxy group and one carboxylic acid group, and combinations thereof.

The advancement reaction may be conducted in the presence or absence of a solvent with the application of heat and mixing. The advancement reaction may be conducted at atmospheric, superatmospheric or subatmospheric pressures and at temperatures of from about 20° C. to about 260° C., preferably, from about 80° C. to about 240° C., and more preferably from about 100° C. to about 200° C.

The time required to complete the advancement reaction depends upon the factors such as the temperature employed, the chemical structure of the compound having more than one reactive hydrogen atom per molecule employed, and the chemical structure of the epoxy resin employed. Higher temperature may require shorter reaction time whereas lower temperature requires a longer period of reaction time. In general, the time for completion of the advancement reaction may range from about 5 minutes to about 24 hours, preferably from about 30 minutes to about 8 hours, and more preferably from about 30 minutes to about 4 hours.

A catalyst may also be added in the advancement reaction. Examples of the catalyst may include phosphines, quaternary ammonium compounds, phosphonium compounds and tertiary amines. The catalyst may be employed in quantities of from about 0.01 percent to about 3 percent, preferably from about 0.03 percent to about 1.5 percent, and more preferably from about 0.05 percent to about 1.5 percent by weight based upon the total weight of the epoxy resin.

Other details concerning an advancement reaction useful in preparing the advanced epoxy resin are provided in U.S. Pat. No. 5,736,620 and in the Handbook of Epoxy Resins by Henry Lee and Kris Neville.

Examples of the curing agents and/or catalysts useful for the curable composition include aliphatic, cycloaliphatic, polycycloaliphatic or aromatic primary monoamines, aliphatic, cycloaliphatic, polycycloaliphatic or aromatic primary and secondary polyamines, carboxylic acids and anhydrides thereof, aromatic hydroxyl containing compounds, imidazoles, guanidines, urea-aldehyde resins, melamine-aldehyde resins, alkoxylated urea-aldehyde resins, alkoxylated melamine-aldehyde resins, amidoamines, epoxy resin adducts, and combinations thereof.

Particularly preferred examples of the curing agent include methylenedianiline; 4,4'-diaminostilbene; 4,4'-diamino-alpha-methylstilbene; 4,4'-diaminobenzanilide; dicyandiamide; ethylenediamine; diethylenetriamine; triethylenetetramine; tetraethylenepentamine; urea-formaldehyde resins; melamine-formaldehyde resins; methylolated urea-formaldehyde resins; methylolated melamine-formaldehyde resins; bisphenols such as bisphenol A; bisphenol F (bis-4-hydroxyphenyl methane); bisphenol S (bis-4-hydroxyphenyl sulfone); TBBA (tetrabromobisphenol A); phenol-formaldehyde novolac resins; cresol-formaldehyde novolac resins; sulfanilamide; diaminodiphenylsulfone; diethyltoluenediamine; t-butyltoluenediamine; bis-4-aminocyclohexylamine; isophoronediamine; diaminocyclohexane; hexamethylenediamine, piperazine; 1-(2-aminoethyl)piperazine; 2,5-dimethyl-2,5-hexanediamine; 1,12-dodecanediamine; tris-3-aminopropylamine; and combinations thereof.

Particularly preferred examples of the curing catalyst include boron trifluoride, boron trifluoride etherate, aluminum chloride, ferric chloride, zinc chloride, silicon tetrachloride, stannic chloride, titanium tetrachloride, antimony trichloride, boron trifluoride monoethanolamine complex, boron trifluoride triethanolamine complex, boron trifluoride piperidine complex, pyridine-borane complex, diethanolamine borate, zinc fluoroborate, metallic acylates such as stannous octoate or zinc octoate and combinations thereof.

For the various embodiments, the curing catalyst may be employed in an amount that will effectively cure the curable composition. The amount of the curing catalyst may also depend upon the polyphenol, epoxy resin, and curing agent, if any, employed in the curable composition.

Generally, the curing catalyst may be used in an amount of from about 0.001 to about 2 percent by weight of the total curable composition. In addition, one or more of the curing catalysts may be employed to accelerate or otherwise modify the curing process of the curable composition.

The curing agent may be employed in conjunction with the polyphenol to cure the curable composition. The amounts of combined curing agent and polyphenol are from about 0.60:1 to about 1.50:1, and preferably from about 0.95:1 to about 1.05:1 equivalents of reactive hydrogen atom collectively in the curing agent and the polyphenol.

AcAc or acac is understood to mean the bidentate acetylacetonate ligand.

As used herein, "cyclododecane trialdehyde" and "trialdehyde" and "trialdehydes" refer to a mixture of the trialdehydes of cyclododecane, which includes all possible isomers, including, for example, the 1,4,8 isomer; 1,4,9 isomer; the 1,5,8 isomer; and the 1,5,9 isomers. All enantiomers and diastereomers are also encompassed by this definition.

1,5,9 trans, trans, cis CDDT is the most common CDDT isomer.

EEW means epoxide equivalent weight, and Tg means glass transition temperature.

EXAMPLES

Example 1

Hydroformylation of Cyclododecatriene at 80° C. and 600 Psig with Catalyst Recycle A 100 mL Hastelloy C Parr reactor was cleaned, dried, and pressure tested with nitrogen at the reaction pressure. In a glove box was prepared a solution of Rh(CO)$_2$(AcAc) (50.5 mg), tris(2,4-di-tert butylphenyl)phosphite (0.660 g), and heptane (15.1 g). The catalyst/ligand solution drawn into a 25 mL gas-tight syringe and the solution was transferred into the Parr reactor. The reactor was purged with syn gas (CO/H$_2$ 50:50, 200 psig) three times. The catalyst mixture was stirred at 600 rpm with 200 psig syn gas at 80-90° C. for 30 minutes to activate the catalyst complex, and then cooled to 25° C. overnight under 200 psig syn gas pressure. The reactor was warmed to 45° C., the syn gas was vented, and cyclododecatriene (34.3 g) was added with a 100 mL gas-tight syringe. The mixture was purged with syn gas then pressurized to 150 psig syn gas. The reaction was heated to 80° C. When the temperature reached 79° C., the syn gas pressure was increased to 600 psig. Samples were removed periodically via a three-way valve and analyzed by GC. The reaction was stopped after 9 hours by cooling to room temperature overnight under 200 psig syn gas and no agitation. The clear lower product phase was collected from the reactor via the sampling line (38.4 g). The catalyst solution was left in the reactor under 130 psig syn gas and room temperature. The syn gas was vented. Additional cyclododecatriene (34.3 g) was added to the reactor via a gas-tight syringe. The reactor was purged with syn gas and pressurized to 600 psig syn gas. The reactor was heated to 80° C. for 6 hours and cooled to room temperature overnight. The next day, the reaction was continued at 80° C. for 3.5 hours. The reaction was cooled to room temperature overnight under 150 psig syn gas and no agitation. The product (49.4 g) was collected through the sample line. The remaining reactor contents of product and catalyst solution were collected and the reactor was cleaned with THF and dried.

Several trialdehyde reaction products were combined and analyzed using GC and NMR. GC analysis of the combined products showed the crude aldehyde contained the mono, bis, and trialdehydes in the following approximate ratio: 1:8:93. A Bruker instrument was used to collect NMR data at 300.13 MHz for proton and 75.47 MHz for carbon. CDCl$_3$ was used as the solvent with TMS internal standard. A 10 second delay (D1) was used in proton experiments used for quantization of aldehyde and olefin.

Internal Standard GC Method for Cyclododecatriene Hydroformylation (Agilent 6850)

Column: J&W DB-1 30 m×0.32 mm I.D.×1.0 μm film thickness capillary column.

Oven: Initial temp: 100° C. (2 min hold), 15° C./min to 300° C. (9.67 min hold).

Run time: 25 minutes; Sample: 200-250 mg sample and 100 mg triglyme (internal standard) in 5 mL toluene; Inlet mode, temp and split ratio: split, 280° C., and 100:1, respectively. Detector (FID) Temperature was 300° C.; Injection volume was 1 uL.

Example 2

Preparation of Polyphenol of Cyclododecane Trialdehyde

Cyclododecane trialdehyde obtained from the hydroformylation of cyclododecatriene was analyzed by gas chromatography demonstrating the following composition: cyclododecatriene (0.15 wt. %), cyclododecane monoaldehyde (0.16 wt. %), cyclododecane dialdehyde (9.52 wt. %) and cyclododecane trialdehyde (88.72 wt. %). Cyclodecane trialdehyde (39.74 g, 0.16 mole, 0.48 aldehyde eq) and molten phenol (301.2 g, 3.2 moles) were added to a 2 L glass three neck round bottom reactor. The reactor was additionally outfitted with an ambient temperature (22° C.) condenser and a thermometer, both affixed to the reactor via a Claisen adaptor, plus an overhead nitrogen inlet, a glass stirring shaft with a Teflon™ (Teflon™ fluorocarbon resin is a trademark of E.I. duPont de Nemours) stirrer blade which was coupled to a variable speed motor to provide mechanical stirring and a thermostatically controlled heating mantle and fan which alternately cooled the reactor exterior.

Overhead nitrogen flow (1 L per min) commenced, followed by heating and stirring. Once the temperature reached 65° C., forming a light amber colored solution, addition of four approximately equal aliquots of 3-mercapto-1-propane sulfonic acid catalyst (total catalyst used was 1.25 g, 0.05 mole % with respect to cyclododecane trialdehyde reactant) commenced into the stirred solution. The initial aliquot of catalyst immediately turned the solution light yellow then back to a darker amber color. The remaining three aliquots of catalyst were added over the next 16 min with maintenance of the 65° C. reaction temperature. The solution in the reactor became dark violet colored 39 min after addition of the final aliquot of catalyst. The reaction temperature was maintained at 65° C. for the next 16.3 hr.

At the end of the reaction time, the reactor contents were added to a 1 L single neck round bottom flask and rotary evaporated using a maximum oil bath temperature of 100° C. to remove the bulk of the unreacted phenol. The solid product recovered from the rotary evaporation was added to a 2 L glass beaker and magnetically stirred with 1 L of boiling DI water followed by filtration over a medium fritted glass funnel to recover the washed solid. Washing of the recovered solid with boiling DI water was repeated followed by HPLC analysis of a sample of the washed product which demonstrated the presence of 2.37 area % residual phenol. An additional washing with DI water did not provide any further decrease in phenol content. The solids were added to a ceramic dish and dried in the vacuum oven at 100° C. for 16 hr, removed, ground to a fine powder (109.41 g) and dried in the vacuum oven for an additional 16 hr to provide the polyphenol of cyclododecane trialdehyde as a reddish tan colored powder (107.00 g). HPLC analysis of a sample of the product demonstrated the presence of 1.89 area % residual phenol. FTIR spectrophotometric analysis of a KBr pellet revealed complete disappearance of the aldehyde carbonyl stretch at 1721.9 cm$^{-1}$ with appearance of strong aromatic ring absorbance at 1610.8 (shoulder at 1595.5) and 1510.2 cm$^{-1}$, broad strong hydroxyl 0-H stretching centered at 3382.3 cm$^{-1}$, and broad strong C—O stretching at 1229.4 (shoulder at 1170.5) cm$^{-1}$. HPLC analysis revealed the polyphenol of cyclododecane trialdehyde included multiple components eluting between 3.24 to 8.30 min (phenol residual eluted at 2.49 min).

For all HPLC analyses, a Hewlett Packard 1090 Liquid Chromatograph was employed using a Zorbax Eclipse® (Agilent) XDB-C8 analytical column (5μ, 4.6×150 mm) with an Eclipse® (Agilent) XDB-C8 analytical guard column (5μ, 4.6×12.5 mm) The columns were maintained in the chromatograph oven at 40° C. Acetonitrile and water (treated with 0.05% aqueous o-phosphoric acid) were used as the eluents and were initially delivered via the pump at a rate of 1.000 mL per min as a 50/50% solution, respectively, changing after 5 min to a 90/10% solution and held therein for the next 15 min. The acetonitrile used was HPLC grade, 100.0% purity (by gas chromatography), with a UV cutoff of 189 nm. The o-phosphoric acid used was nominally 85% pure (actual assay 85.1%). The water used was HPLC grade. A diode array detector employed for the sample analysis was set at 225 nm and the reference was set at 550 nm.

Example 3

Preparation of a Curable Powder Composition and Curing of an Epoxy Resin with Polyphenol of Cyclododecane Trialdehyde Diglycidyl ether of bisphenol A [D.E.R.™ 330, Trademark of The Dow Chemical Company ("Dow") or an affiliated company of Dow] (5.0696 g, 0.02836 epoxide eq) was added to a 100 mL glass beaker additionally containing a magnetic stir bar. The diglycidyl ether had an EEW of 178.75. All weighing was completed on scales with 4 place accuracy. Heating and stirring of the diglycidyl ether to 150-160° C. commenced followed by the addition of polyphenol of cyclododecatriene trialdehyde (3.6338 g, 0.02836 hydroxyl eq) from Example 2 in eight approximately equal aliquots. Each aliquot was allowed to dissolve before the addition of the next aliquot. The resultant amber colored solution was cooled to 23° C. to provide a solid which could be ground to a powder product.

A portion (4.0074 g) of the powder blend of the diglycidyl ether and polyphenol of cyclododecatriene trialdehyde was added to an aluminum dish and placed in an oven preheated to 120° C. A solution of 2-methylimidazole (0.2006 g) in cyclohexanone (2.0160 g) was prepared and warmed to maintain the solution state. A single drop (0.0165 g) of the 2-methylimidazole solution was added to the molten blend of diglycidyl ether and polyphenol of cyclododecatriene trialdehyde followed by vigorous stirring, providing 0.41 mg of 2-methylimidazole per g of blend. Approximately 0.1 g of the 2-methylimidazole catalyzed blend was immediately removed and cooled to 23° C. to provide a sample for DSC analysis. The remaining blend was cured by placing the aluminum dish in an oven which had been preheated to 200° C. for 2 hr.

For analysis of curing, a DSC 2910 Modulated DSC (TA Instruments) was employed, using a heating rate of 7° C. per min from 0° C. to 350° C. under a stream of nitrogen flowing at 35 cubic centimeters per min, with holding at 0° C. for 2 min. For a portion (9.6 mg) of the 2-methylimidazole catalyzed blend, a 217.7° C. onset to cure was detected, followed by a cure exotherm having a maximum of 300.9° C. and an enthalpy of 192.2 J/g, and an end of cure of 315.6° C.

DSC analysis of a portion (27.0 mg) of the product cured at 200° C. was completed using a heating rate of 7° C. per min from 0° C. to 325° C. under a stream of nitrogen flowing at 35 cubic centimeters per min, with holding at 325° C. for 5 min. The first scanning detected an exotherm with a 205.2° C. onset, an exotherm with a maximum of 290.7° C. and an enthalpy of 66.5 J/g, and an end of 312.7° C. This exotherm was attributed to additional curing. Second, third and fourth scannings were featureless, with no Tg detected up to the 325° C. maximum temperature for the DSC analysis.

Example 4

Repeat of Preparation of a Curable Powder Composition and Curing of an Epoxy Resin with Polyphenol of Cyclododecane Trialdehyde Example 3 was repeated using diglycidyl ether of bisphenol A (5.4939 g, 0.03074 epoxide eq) and polyphenol of cyclododecatriene trialdehyde (3.9379 g, 0.03074 hydroxyl eq) from Example 1. A portion (4.0010 g) of the powder blend of the diglycidyl ether and polyphenol of cyclododecatriene trialdehyde was catalyzed with 2-methylimidazole solution (0.0210 g) using the method of Example 3, providing 0.52 mg of 2-methylimidazole per g of blend. Approximately 0.1 g of the 2-methylimidazole catalyzed blend was immediately removed and cooled to 23° C. to provide a sample for DSC analysis. The remaining blend was cured by placing the aluminum dish in an oven which had been preheated to 200° C. for 2 hr.

DSC analysis of curing was repeated using the method of Example 3. For a portion (11.2 mg) of the 2-methylimidazole catalyzed blend, a 212.7° C. onset to cure was detected, followed by a cure exotherm having a maximum of 298.0° C. and an enthalpy of 240.7 J/g, and an end of cure of 311.8° C.

DSC analysis of a portion (25.6 mg) of the product cured at 200° C. was completed using the method of Example 3. The first scanning detected an exotherm with a 196.53° C. onset, an exotherm with a maximum of 293.2° C. and an enthalpy of 94.5 J/g, and an end of 312.2° C. This exotherm was attributed to additional curing. Second, third and fourth scannings were featureless, with no Tg detected up to the 325° C. *maximum* temperature for the DSC analysis.

Comparative Example A

Preparation of a Curable Composition and Curing of an Epoxy Resin with a Phenolic Curing Agent Comparative Example A was completed using diglycidyl ether of bisphenol A [D.E.R.™ 330] (5.4939 g, 0.03074 epoxide eq) and D.E.H.™ 85 (7.4338 g, 0.02859 hydroxyl eq) and the method of Example 3. D.E.H.™ 85 is a phenolic curing agent based on an unmodified solid reaction product of liquid epoxy resin and bisphenol A available from The Dow Chemical Company or an affiliate thereof. The resultant yellow colored solution was cooled to 23° C. to provide a solid which could be flaked but sintered on standing.

A portion (4.0002 g) of the blend of the diglycidyl ether and D.E.H.™ 85 was catalyzed with 2-methylimidazole solution (0.0206 g) using the method of Example 2, providing 0.51 mg of 2-methylimidazole per g of blend. Approximately 0.1 g of the 2-methylimidazole catalyzed blend was immediately removed and cooled to 23° C. to provide a sample for DSC analysis. The remaining blend was cured by placing the aluminum dish in an oven which had been preheated to 200° C. for 2 hr.

DSC analysis of curing was repeated using the method of Example 3. For a portion (10.4 mg) of the 2-methylimidazole catalyzed blend, a 94.9° C. onset to cure was detected, followed by a cure exotherm having a maximum of 177.0° C. and an enthalpy of 107.2 J/g, and an end of cure of 221.8° C.

DSC analysis of a portion (33.3 mg) of the product cured at 200° C. was completed using the method of Example 3. The first scanning detected a Tg of 101.9° C. Second, third and fourth scannings detected a Tg of 100.5° C., 99.8° C., and 99.8° C., respectively.

Example 5

Preparation of a Curable Powder Composition and Curing of an Epoxy Resin with Polyphenol of Cyclododecane Trialdehyde Using Increased 2-Methylimidazole Catalyst A. Use of 1.25 mg of 2-Methylimidazole Per g of Blend of Epoxy Resin with Polyphenol of Cyclododecane Trialdehyde Example 3 was repeated using diglycidyl ether of bisphenol A (4.4911 g, 0.02513 epoxide eq) and polyphenol of cyclododecatriene trialdehyde (3.2191 g, 0.02513 hydroxyl eq) from Example 2 in eight approximately equal aliquots. A portion (2.5839 g) of the blend of the diglycidyl ether and polyphenol of cyclododecatriene trialdehyde was catalyzed with 2-methylimidazole solution prepared by dissolving 2-methylimidazole (0.0032 g) in cyclohexanone (0.032 g) providing 1.25 mg of 2-methylimidazole per g of blend. Approximately 0.1 g of the 2-methylimidazole catalyzed blend was immediately removed and cooled to 23° C. to provide a sample for DSC analysis.

DSC analysis of curing was repeated using the method of Example 3. For a portion (11.9 mg) of the 2-methylimidazole catalyzed blend, a 90.0° C. onset to cure was detected, followed by a cure exotherm having a maximum of 169.3° C. and an enthalpy of 52.0 J/g, and an end of cure of 201.9° C. A second cure exotherm was detected with a 207.7° C. onset to cure, followed by a cure exotherm having a maximum of 304.0° C. and an enthalpy of 120.4 J/g, and an end of cure of 323.0° C. A second scanning was featureless, with no Tg detected up to the 325° C. maximum temperature for the DSC analysis.

B. Use of 2.5 mg of 2-Methylimidazole Per g of Blend of Epoxy Resin with Polyphenol of Cyclododecane Trialdehyde A portion (2.1841 g) of the blend of the diglycidyl ether and polyphenol of cyclododecatriene trialdehyde from A. above was catalyzed with 2-methylimidazole solution prepared by dissolving 2-methylimidazole (0.0055 g) in cyclohexanone (0.055 g) providing 2.5 mg of 2-methylimidazole per g of blend. Approximately 0.1 g of the 2-methylimidazole catalyzed blend was immediately removed and cooled to 23° C. to provide a sample for DSC analysis.

DSC analysis of curing was repeated using the method of Example 3. For a portion (9.3 mg) of the 2-methylimidazole catalyzed blend, a 86.6° C. onset to cure was detected, followed by a cure exotherm having a maximum of 190.4° C. and an enthalpy of 58.8 J/g, and an end of cure of 233.0° C. A gradual exothermic shift in the baseline was detected with a 252.9° C. onset. A second scanning was featureless, with no Tg detected up to the 325° C. maximum temperature for the DSC analysis.

Example 6

Preparation of a Curable Powder Composition and Curing of an Epoxy Resin with Polyphenol of Cyclododecane Trialdehyde and Phenolic Curing Agent Mixture Example 3 was repeated using diglycidyl ether of bisphenol A (5.4456 g, 0.03047 epoxide eq), polyphenol of cyclododecatriene trialdehyde (0.9785 g, 0.007616 hydroxyl eq) from Example 2 and D.E.H.™ 85 (5.9407 g, 0.022849 hydroxyl eq) from Comparative Example A. A portion (4.0345 g) of the powder blend of the diglycidyl ether, polyphenol of cyclododecatriene trialdehyde and D.E.H.™ 85 was catalyzed with 2-methylimidazole solution (0.0219 g) using the method of Example 3, providing 0.54 mg of 2-methylimidazole per g of blend. Approximately 0.1 g of the 2-methylimidazole catalyzed blend was immediately removed and cooled to 23° C. to provide a sample for DSC analysis. The remaining blend was cured by placing the aluminum dish in an oven which had been preheated to 200° C. for 2 hr.

DSC analysis of curing was repeated using the method of Example 3. For a portion (12.6 mg) of the 2-methylimidazole catalyzed blend, a 91.6° C. onset to cure was detected, followed by a cure exotherm having a maximum of 178.7° C. and an enthalpy of 158.8 J/g, and an end of cure of 223.9° C.

DSC analysis of a portion (34.3 mg) of the product cured at 200° C. was completed using the method of Example 3. First, second, third and fourth scannings revealed Tg's of 104.7° C., 108.9° C., 108.6° C., and 108.1° C., respectively.

What is claimed is:

1. Methods of making compounds of the formula:

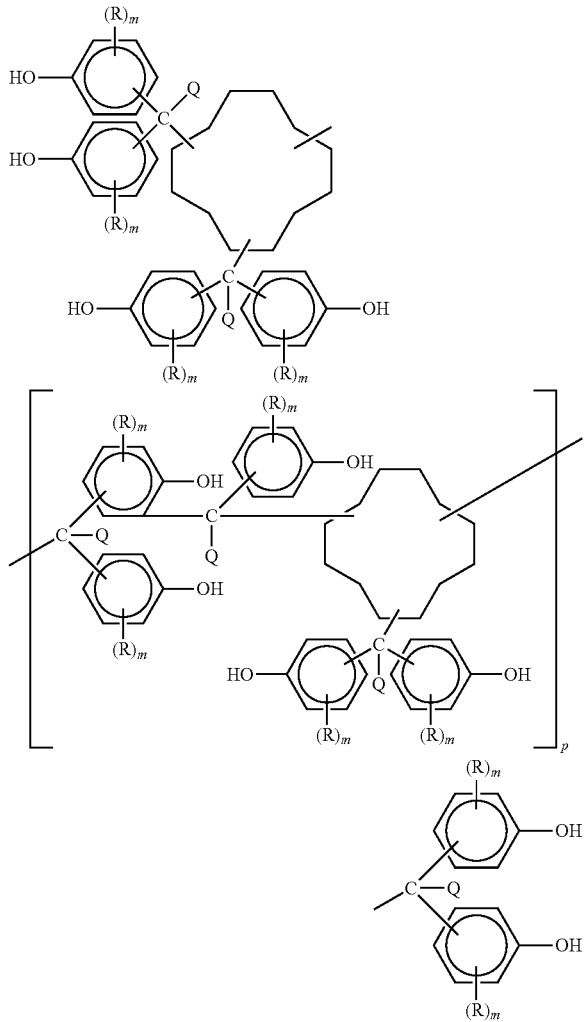

wherein each m independently has a value of 1 to 3, p has a value of zero to 20;

each R is independently halogen, nitrile, nitro; $C_1$-$C_6$ alkyl or $C_1$-$C_6$ alkoxy, wherein the alkyl and alkoxy groups are optionally substituted with one or more halogen atoms, $C_2$-$C_6$ alkenyl or $C_2$-$C_6$ alkenyloxy groups; and each Q is independently hydrogen or $C_1$-$C_6$ alkyl; or the R group may be a $C_3$-$C_4$ alkylene group that optionally contains one or two double bonds and is bonded to two adjacent carbons on the ring to which it is attached;

the methods comprising
subjecting the trialdehyde of cyclododecane to conditions sufficient to convert the aldehyde groups to the diphenolmethyl groups.

2. Methods according to claim 1, wherein the trialdehyde is reacted with an optionally substituted phenol in the presence of a catalyst.

3. Methods according to claim 1, wherein the conditions comprise a reaction temperature of 50° C. to 80° C. and a reaction time of 10 hours to 24 hours and the catalyst is acidic.

4. Methods according to claim 2, wherein the catalyst is 3-mercapto-1-propane sulfonic acid.

* * * * *